(12) United States Patent
Scaringe et al.

(10) Patent No.: US 6,576,473 B1
(45) Date of Patent: Jun. 10, 2003

(54) REMOVABLE TEST KIT AND METHOD OF USE FOR VAPOR COMPRESSION SYSTEMS

(75) Inventors: Robert P. Scaringe, Rockledge, FL (US); Lawrence R. Grzyll, Merritt Island, FL (US); Dwight D. Back, Palm City, FL (US); John A. Meyer, Palm Bay, FL (US); Gregory S. Cole, Ormond Beach, FL (US)

(73) Assignee: Mainstream Engineering Corporation, Rockledge, FL (US)

( * ) Notice: Subject to any disclaimer, the term of this patent is extended or adjusted under 35 U.S.C. 154(b) by 0 days.

(21) Appl. No.: 09/321,085

(22) Filed: May 28, 1999

(51) Int. Cl.$^7$ .......................... G01N 21/81; G01N 21/77
(52) U.S. Cl. .......................... 436/169; 436/167; 436/39; 422/58; 422/61; 422/102; 422/104; 422/86
(58) Field of Search ................ 422/61, 83, 86, 422/58, 100, 102–104; 436/164, 167, 169, 177, 39

(56) References Cited

U.S. PATENT DOCUMENTS 4,923,806 A * 5/1990 Klodowski .................. 436/39
5,071,768 A * 12/1991 Klodowski .................. 436/39
5,363,661 A * 11/1994 Condit et al. ................ 422/83

FOREIGN PATENT DOCUMENTS

WO      96/33394      * 10/1996

* cited by examiner

Primary Examiner—Lyle A. Alexander
(74) Attorney, Agent, or Firm—Crowell & Moring LLP

(57) ABSTRACT

A field-installable and removable moisture and/or acid test kit and method is used for a vapor compression system. A moisture and/or acid indicator is provided in the test kit which is installed at a single point location upstream or downstream of the system compressor in a region where the system working fluid is in a substantially vapor phase. The test kit can be connected to the system by a threaded connection or a quick disconnect fitting. The moisture/acid indicator in the test kit detects the presence of moisture and/or acid by a diffusion of moisture or acid to the indicator via diffusion. Some magnification is provided in the test kit because the lower transport rates from the vapor diffusion mechanism requires a smaller mass of indicator material than has been used in conventional flowing liquid systems.

40 Claims, 3 Drawing Sheets

REMOVABLE TEST KIT AND METHOD OF USE FOR VAPOR COMPRESSION SYSTEMS

BACKGROUND OF THE INVENTION

The present invention relates to a simple field installable/removable moisture and/or acid indicator or test kit, and more particularly, to a moisture and/or acid test indicator or test kit used in a vapor compression system and the like which can be attached to the system via an existing Schrader-type service valve making the indicator easily installed and/or replaced in the field, without the need to isolate a section of the system, recover the trapped refrigerant, install the indicator into the system, and recharge the section previously isolated and evacuated. The indicating material substance or formulation of the present invention is held in a transparent fixture which when tightened on the service valve, automatically depresses the Schrader valve core allowing refrigerant to contact the indicator material. This indicator can also be configured to magnify the section of the device which contains the indicator material. This allows technicians in the field to easily, simply, quickly and inexpensively attach a moisture or test kit, or change the test kit, on a fully charged and operating system without the need to interrupt operation of the system.

The presence of moisture in the refrigerant of vapor compression refrigerators, heat pumps, and air conditioners (generally referred to as, the system) can lead to the formation of ice crystals in the throttling device, thereby restricting the flow of refrigerant and decreasing capacity. The presence of water in such a system also accelerates the formation of acids in the system which severely shorten the life of both the compressor and the refrigerant.

All systems typically have service valves with valve core depressors (often referred to as Schrader-valves). These valves, like automobile tire-valves, are opened when a valve core is depressed, usually by the device being attached to the valve. For refrigeration systems, these types of service valves with valve core depressors are used in several standard sizes, with ¼" being the most common and ⅜", ½", and and ⅝" also used.

Checking the system for moisture is a common maintenance procedure. Due to cost cutting measures, however, many systems do not contain a traditional moisture indicator in the system. When such a moisture indicator is inherent in the system it is typically located in the liquid line or in the liquid receiver as part of a liquid sight glass. Such indicators are configured for liquid refrigerant to flow through the device. Alternatively, U.S. Pat. Nos. 4,923,806 and 5,071,768, disclose a device which attaches to the service valve and allows refrigerant to flow through the device and into the ambient surroundings, indicating both moisture and acid as the refrigerant is vented to the environment. In addition to the obvious disadvantage of venting refrigerant into the environment, this device can not be installed for extended periods due to the constant flow of refrigerant being vented.

Visual sensors or indicators for use in detecting the moisture of a refrigerant in a vapor compression system are known, as seen for example, in U.S. Pat. No. 4,018,061 as well as in commercial products. A permanently installed sensor has a sight glass or window through which moisture content is determined by viewing a color-change indicator. Cobaltous chloride and cobaltous bromide are well known in the art as a moisture indicating chemicals, with the former changing from blue to pink when wet and the latter changing from green to yellow when wet.

Visual sensors or indicators for use in detecting the corrosive state of a fluid in a heat exchanger system are known as seen, for example, in U.S. Pat. No. 5,127,433. A permanently installed sensor has a sight glass or window through which corrosiveness or moisture content is determined by viewing a flap or ball displaying a color indicating either the need to change the fluid or to add corrosion inhibitors. Alternatively, corrosiveness can be indicated by a ruptured or broken diaphragm located between the sight glass and the fluid.

Humidity and corrosion indicators for packaged goods in which a thin cobaltous chloride film is used as the sensing element are discussed in U.S. Pat. No. 3,084,658. An elastomeric grommet sealed by a transparent disk is inserted into an opening in a package wall. A disk impregnated with the cobaltous chloride is secured beneath a window and can be replaced.

With respect to closed refrigeration systems, other types of indicator systems are known for testing the presence and concentration of contaminants in a refrigerant. For example, U.S. Pat. Nos. 4,923,806 and 5,071,768 show apparatus for testing liquid or vapor contaminants in a closed system regardless of whether or not the apparatus is operating. A disposable testing tube made of transparent material is used at the end of a compressor discharge line or elsewhere in the system. One section of the tube is provided with water removal and moisture indicating chemicals, such as cobaltous chloride and another section is provided with acid indicating chemicals such as a solution of bromophenol blue, ethanol and glycerol. This known construction is relatively complicated and requires a separate, specially configured flow restrictor in addition to a tube holder, and an expensive testing tube in which the multiple contaminant testing chemicals and filter screens are permanently located. U.S. Pat. No. 4,018,061 describes a moisture-indicating device in contact with flowing liquid refrigerant. This device is an integral part of the refrigeration system, and as such, the system must be shut down in order to install the device.

Likewise, U.S. Pat. No. 5,377,496 shows an acid contamination indicator for closed loop vapor compression refrigeration systems in which the indicator is permanently or removably installed in the bypass line around the system compressor where the refrigerant is always in the gaseous phase. A casing has a visual indicator bed of bromophenol blue as the acid indicating medium which is contacted by the refrigerant after flowing through a filter and a flow restrictor orifice. Porous retainer disks are held against the bed by springs. Moreover, the indicator, which changes color when exposed to acids or bases, are solid, and they must be exposed to the test stream in some fashion. Accordingly, this solid indicator must be mixed with an inert substance to provide some porosity, contact surface area, and increased volume and then packaged in a clear tube. The vapor refrigerant is then passed through the porous mixture arranged in a bypass loop between the suction and discharge ends of a compressor or in the main refrigerant flow path between the compressor discharge and a heat exchanger to observe a color change. Again, we have recognized that this is an unduly complicated construction which requires a substantial outlay for production and installation. A bypass of refrigerant from the compressor discharge to the compressor suction reduces the capacity and performance of the vapor compression system as well as increases the compressor operating temperature since hot discharge vapor is reintroduced into the compressor suction.

Pending U.S. patent application Ser. No. 08/423,211, filed Apr. 17, 1995, assigned to Mainstream Engineering Corporation of Rockledge, Fla. discloses yet another way of detecting the presence of acid in a refrigeration system, with an indicating device configured to temporally flow refrigerant through it and vent this refrigerant to the environment. The disclosure of that application is incorporated by reference herein.

Yet another type of contaminant detector is marketed by Refrigeration Technologies of Fullerton, Calif. under the trademark "CHECKMATE". A specific volume of gas passes through a detection tube at a predetermined termination pressure. However, a sealed Pyrex detection tube containing a color-changing chemical and having ends which are pierced when fully assembled can only be used once even when the test is negative, and thus this approach entails considerable expense regardless of its technical merits.

It should be pointed out that all the prior art for moisture or other contamination measuring devices, whether permanent or temporary, have one thing in common, namely an inlet and outlet so that refrigeration passes through the device. The refrigerant which passes through is (a) vented to ambient air or (b) by-passed to another portion of the system, or (c) the device is permanently placed in the refrigerant system's normal flow path. We realized that due to cost saving measures, many air conditioning systems do not have a moisture indicator in the system, and it is expensive and disruptive to the unit's operation, to retrofit such an indicator in the field.

In a vapor-compression system, refrigerant flows from the condenser to the expansion valve, where it flashes into a two-phase mixture and then enters the evaporator. Superheated refrigerant vapor, with some entrained oil, leaves the evaporator and is compressed in the compressor, before being condensed in the condenser to complete the cycle. The presence of water in the system, which is a very real possibility, can result in the formation of ice crystals as the refrigerant is throttled in the expansion device. Because the expansion device is a significant flow restriction, ice formed there can clog the flow path completely stopping the flow of refrigerant or severely reducing capacity. In addition to reducing system capacity, the ice formation can result in excessive pressures and system shut down. If this were to occur, the ice blockage would typically melt, allowing the system to restart and operate normally until the ice again formed. This overall result would be an on-off cycling of the device. Moisture can also accelerate the formation of corrosive acids in the system.

SUMMARY OF THE INVENTION

While we have looked at a temporary flow through indication device for moisture, the problem is compounded by the fact that the moisture levels attempting to be measured (at about 100 PPM or less) are significantly lower than the moisture level in ambient air. The costs associated with manufacturing a moisture indicator in this relatively wet environment and the false reading associated with exposing the indicator to ambient air before using, have led us to recognize a different solution to the problem. That is, a field installable temporary test kit device is used which does not begin as a dry indicator but rather begins at equilibrium with moisture in the air and therefore indicates wet conditions when first installed but after exposure to the refrigeration system reaches an equilibrium moisture concentration thereby indicating the level of moisture in the system.

Rather than constructing a device with an inlet and outlet that must be plumbed into the system (at a considerable cost), or one that must by-pass refrigeration in the system (thereby reducing performance and increasing compressor suction-side refrigerant temperature), however, we have configured a removable test kit with a single connection point which temporarily connects to the existing system service port (with only the tightening of a wrench in the case of a threaded service port, or by pushing it on, in the case of a quick disconnect type of service port.

Our device does not degrade system performance and can be quickly and easily installed. The action of attaching the indicator of the present invention to the service valve depresses the service valve's Schrader valve, thereby allowing vapor refrigerant of the system to contact the indicator chemical. This is a particularly advantageous element of the present invention, because it affords the user with the benefits of a permanent moisture indicator, namely, sufficient time for the indicator to reach equilibrium moisture conditions (regardless of the starting moisture level), as well as the benefits of a low cost field-test device. That is, it can be used on an operating system without opening the system or disturbing its operation in any way.

The indicator housing of the present invention mechanism has a mechanism for depressing the Schrader valve core and a structure for holding an indicator material. The indicator formulation can be impregnated on a paper or porous plastic sheet or can be a paint applied to the interior surface of the cap. The moisture indicator material is prepared from an aqueous or solvent solution of finely divided particles of the indicator chemical and optionally polymers, and optionally other hygroscopic compounds. The paint is characterized by one color when in the absence of significant amounts of water and by a gradual color change to a second color with the presence of increasing quantities of water. The indicator housing is constructed of a clear material (or a material with a window), and can incorporate a magnifying glass (either manufactured into the clear material or into the window) so that the color change can be easily seen without a large quantity of the indicator material. This magnification is needed because the lower transport rates resulting from a vapor diffusion process require a smaller mass of indicator material compared with a flowing liquid system of the types described above to reach equilibrium moisture conditions in a practical time period.

Other known moisture indicators with an inlet and outlet, either temporary or permanent, have the moisture indicating material in the liquid stream of refrigerant, whereas the indicator of the present invention is located in a service valve fitting so that refrigerant (mostly vapor) does not flow through the device. Consequently, moisture must diffuse through the relatively stagnant area between the refrigerant flow path and the location of the indicator material. The smaller the mass of indicator material, the smaller the quantity of moisture that must diffuse before a complete reaction is achieved.

Because the mechanism of the moisture transport in the present invention is diffusion instead of flowing the refrigerant past the indicator material, an experiment was performed to verify that the diffusion of moisture from refrigerant into the adsorbent material could be accomplished in a reasonably short time. The experiment determined if diffusion of the moisture through static refrigerant would be rapid enough to be practical. Refrigerant samples were formulated with increasing quantities of moisture (ranging from 3 PPM water to 900 PPM in the liquid refrigerant). These samples were then exposed to moisture laden (pink) cobalt chloride-containing indicator materials, and moisture indicator observations were continued on a regular basis with time and indicator color recorded. Once the indicators had stabilized (remained the same color for a period greater than two days), the vapor and liquid were both tested for moisture by using a Karl Fisher coulometric titrator.

Although there is no generally accepted maximum permissible moisture limit on operating systems, a level of 125 ppm is an approximate upper limit for moisture concentrations in refrigerants found in systems (centrifugal chillers down to small unitary systems) operating for 10 years or more. We have also found through Karl Fisher titration that for refrigerants HFC-134a and HCFC-22 the percent by weight of water in the vapor phase relative to that in the liquid phase at equilibrium ranges from about 0.25–1, and is a function of temperature and the total concentration of moisture in the vapor/liquid system. This ratio is a thermodynamic property of the refrigerant and water system and can be very different for other refrigerants.

Results from this experiment indicate that the diffusion rates are sufficient, even in static conditions, to invoke a color change within a reasonable period of time (one day or less). To notice any color change in systems containing less than 100 PPM (parts per million) moisture in the liquid refrigerant, about one hour was required. After about fifteen hours, the color change was observed to be essentially complete (greater than 90% complete) for all moisture levels tested. Since the color change approaches an equilibrium in an exponential manner, a substantial (at least ⅔ color change) change can be seen within 8 hours. This degree of color change is clearly significant enough for a refrigeration technician to accurately diagnose a moisture contamination problem.

We have discovered that a device can be configured, either from a clear material or with a window, to contain a connection to the service valve, to depress the service valve, to hold the moisture indicating material, to magnify the moisture indication material so that a color change can be seen with a smaller mass of material, and a simple connection to an existing service port on the system so that the device can be attached without disturbing the system in any way. This temporary device can be easily removed when normal access to the service port is needed and can be easily changed when excessive moisture levels have made it no longer usable.

The device according to the present invention allows for testing with the system on or off. In addition, it does not have to be installed in a line but rather is temporarily or permanently connected to existing service connections, for example, to a Schrader-valve which is not directly in the flow path of the refrigerant. This is a surprising discovery because indicators are traditionally located in the liquid flow path or if connected to a vapor service valve vent to ambient or to another part of the system so as to have refrigerant flow through the device.

Specifically our invention currently contemplates use of an indicator chemical such as cobaltous chloride ($CoCl_2$) or cobaltous bromide ($CoBr_2$). $CoCl_2$ will hydrate with six water molecules changing from blue color to pink color. $CoBr_2$ will hydrate with six water molecules changing from green color to yellow color. There are also other chemicals which change color upon hydration including copper sulfate and other cobalt compounds. Certain alkali metal ozonides also change color. Acid-base reactions can also be used in conjunction with proper indicators in the presence of water.

Thus, the present invention takes advantage of the difficulty of normally attaching a permanent indicator into the plumbing of a existing (working) system and the cost and inconvenience of using a temporary indicator which vents or by-passes refrigerant to achieve the necessary flow through the indicator.

While many commercial moisture indicator chemicals are available, the preferred embodiment of this invention will use $CoCl_2$ as the moisture indicator chemical. If the moisture concentration is not enough to turn the indicator completely pink, however, an intermediate color, between blue and pink (pale, almost while) will be observed. Therefore, the intensity of the change depends on what percentage of the indicator has been transformed (reacted) to the wet form. If the $CoBr_2$ indicator is used a wet environment will produce a yellow color, where as in a dry environment the indicator chemical will appear green. If the moisture concentration is not enough to turn the indicator completely yellow, however, an intermediate color, between green and yellow (that is some yellowish shade of green) will be observed. Therefore, the intensity of the color change depends on what percentage of the indicator has been transformed (reacted) to the wet form.

Hygroscopic modifiers can also be added to the moisture sensing formulation in order to increase or decrease the sensitivity of the device to moisture present in the refrigeration system working fluid. These materials can include hygroscopic compounds such as copper sulfate, zinc chloride, calcium chloride, and silica gel or polymers which absorbs certain levels of moisture such as cellulose acetate, cellulose acetate butyrate, polyvinyl alcohol, and polyamide polymers.

It is, therefore, an object of the present invention to provide an accurate, yet simple and inexpensive, test device which can indicate the refrigerant's moisture and/or acid level by contact with refrigerant vapor from existing system service valves, without the need to flow the refrigerant through the device, to provide an indication of the condition of the refrigerant and therefore the condition of the system.

The present invention advantageously uses a readily available, inexpensive indicator held in a transparent cap-like fixture to monitor the moisture and/or acid level. The indicator chemical reaction is essentially a function of moisture and/or acid level because the indicator material is kept in place until equilibrium conditions are reached. The present invention attaches to a standard refrigeration service valve with or without a valve-core depressor (Schrader-valve).

For automotive air conditioning applications, moisture and/or acid problems also exist. In fact, because of the frequent refrigerant recharging of automobile systems, the moisture problems are even worse. The present invention can also be used in those applications; however, the service port on newer automobiles is not threaded but rather uses a quick disconnect which by EPA Clean Air Act regulations is different for each refrigerant being used in an automobile application. The high-side and low-side ports are also different to avoid confusion by the technician or equipment owner. The indicator device of the present invention can be configured to securely attach to these different fittings (reference Fitting Sizes for Motor Vehicle Refrigerants June 1997, EPA-430-F-97-067).

BRIEF DESCRIPTION OF THE DRAWINGS

These and other objects, features and advantages of the present invention will become more readily apparent from the following detailed description thereof when taken in conjunction with the accompanying drawings wherein.

DETAILED DESCRIPTION OF THE DRAWINGS

Figure 1:
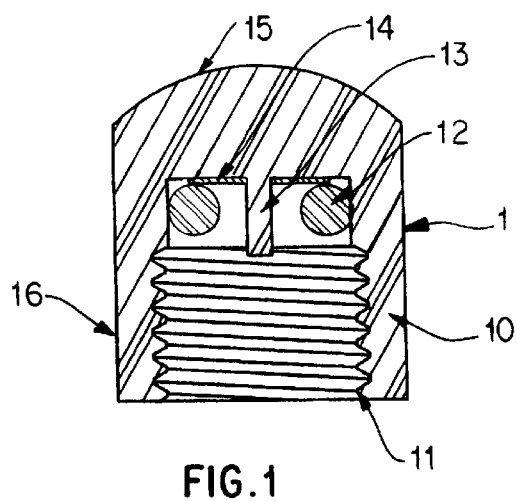
FIG. 1 is a cross-sectional elevational view of one embodiment of the indicator cap in accordance with the present invention.
Figure 2:
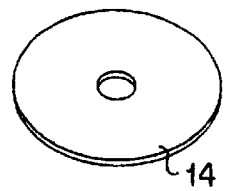
FIG. 2 is an isolated perspective view of the indicator material, configured as a ring, which is located over the valve core depressor and secured.

Referring now to FIG. 1, the indicator is indicated generally by reference numeral 1 and comprises a cap-shaped member 10, having an internal thread 11, a sealing O-ring 12, a valve core depressor 13 formed by a protruding portion from the inner surface of the cap 10, an indicator material 14 in the form of a washer as seen in FIG. 2. An upper or outside surface 15 of the cap member 10 is shaped to provide magnification and the sides 16 are configured as flat surfaces for tightening the indicator. We have found several important considerations which must be taken into account in selecting a material for the cap member 10. First, the material selected for the cap must be compatible with refrigerants (e.g. R-12, R-22, R-134a, R-502, etc.), lubricating oils (e.g. mineral oil, POE, alkyl benzene, PAG, etc.), and mating fittings. Second, the material must be strong enough to withstand internal pressure of the a/c or refrigeration system. Third, the material must have high light transmittance so that the indicator material inside the cap is clearly visible to the user of the product. Fourth, it should be made from an injection mold-grade of plastic to lessen manufacturing costs. Several plastics, such as clear grade nylon and PET, can be used for this purpose. However, the principles of the present invention can also be carried out with a variety of other materials if certain trade-offs are acceptable.

The indicator material 14 includes a standard or known indicator chemical and is pinched or sandwiched between the inner surface of the cap 10 and the O-ring 12. The indicator material 14 can, for example, be produced by preparing a solution of 87% acetone, 3% cellulose acetate, 3% $ZnCl_2$ and 7% $CoCl_2$. Another formulation used to produce the indicator material was a solution of 79% acetone, cellulose acetone 5% ZnCl and 13% $CoCl_2$. A porous paper is then dipped into the solution and then allowed to dry for about 10 minutes. After the porous material has dried, the paper is a pink color indicating the moisture present in the air. The acetone solvent is used to dissolve the polymer and other components in the formulation and will differ with the use of other polymers. Other useful solvents could include alcohols and water. Furthermore, the porous paper can also be impregnated with an acid indicating formulation.

Figure 4:
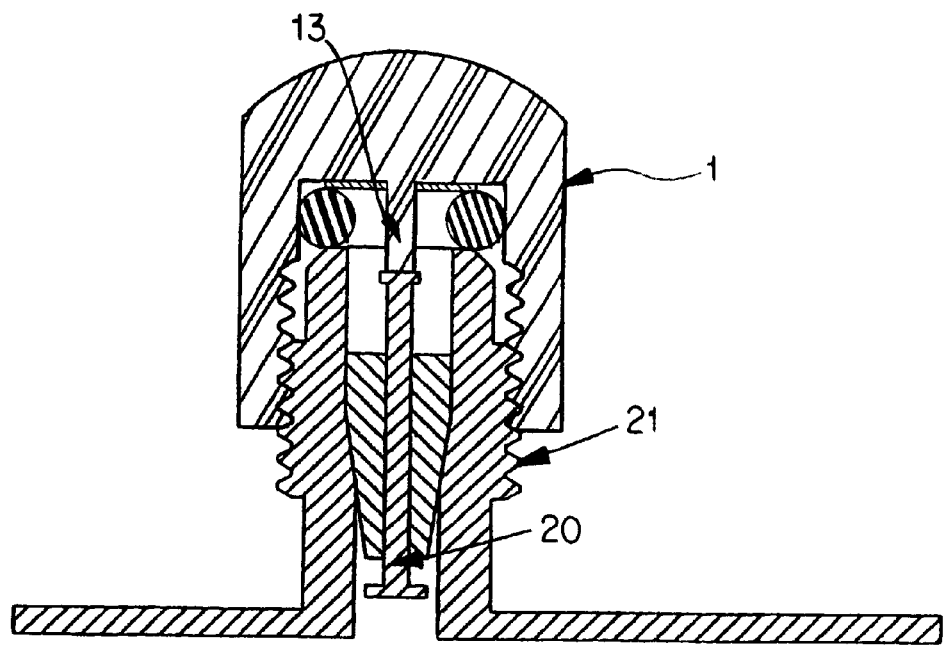
FIG. 4 is a view of the indicator cap of FIG. 1 installed on a refrigeration service valve which uses a Schrader valve.

The washer-shaped moisture indicator insert 14 fitted or impregnated with moisture and/or acid reacting formulation is inserted into the cap 10 to sit against the flat inner surface and is secured with the O-ring 12. The O-ring 12 is held in place by a slight compressive load on the O-ring, aided by friction, and optionally a small machining relief below the last thread 11. As shown in FIG. 4, the valve core depressor 13 is advantageously used to depress a valve core 20 of the system's vapor service valve 21 (when present) which opens the valve service port and allows refrigerant vapor to contact the indicator. The external clear magnifying portion 15 of the indicator 1 allows a smaller mass of indicator material 14 to be used.

Figure 5:
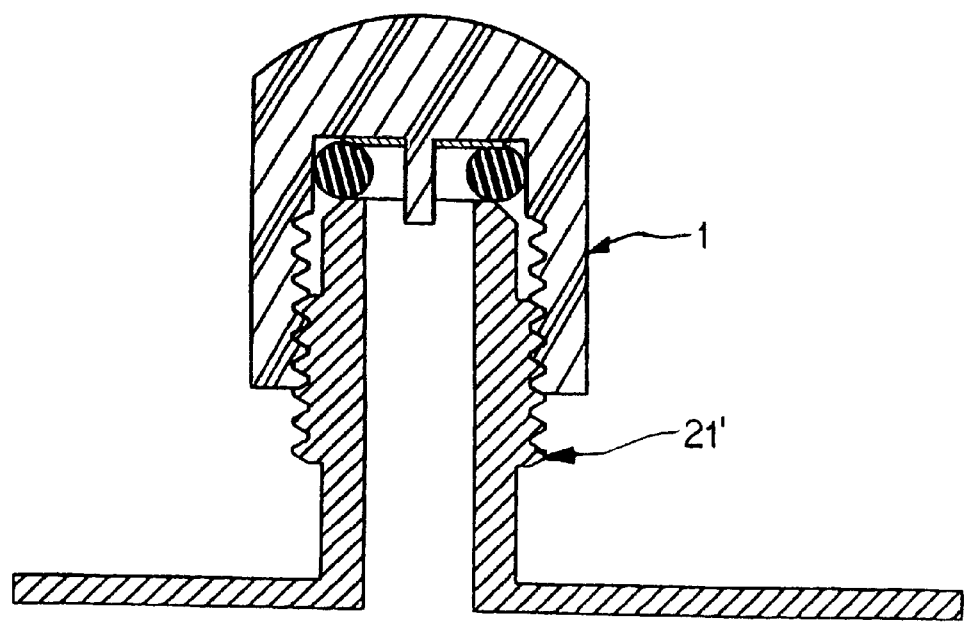
FIG. 5 is a view of the indicator cap of FIG. 1, but installed on a service valve which does not use a Schrader valve to access the system.

Alternatively, as seen in FIG. 5, the valve core depressor 13 has no function when used with a service valve 21' which does not have a valve core of the type shown in FIG. 4. The total test time is dependent on the diffusion of components in the vapor phase through the service port allowing an equilibrium concentration to be achieved. This equilibrium has been found to be typically achieved in less than 1 day. Refrigerant vapor, not liquid, is exposed to the indicator material by attaching the indicator against the system's vapor service valve 21, 21', typically the valve on the compressor suction or inlet side.

In one embodiment of the present invention, the moisture indicator is allowed to become wet due to exposure with ambient conditions during manufacturing to reduce manufacturing costs significantly. This excess moisture must, however, diffuse from the indicator and into the refrigerant before an equilibrium concentration is achieved (the actual moisture added to the system is insignificant due to the relative mass of the indicator and refrigerant). This approach results in a slower moisture indication compared to starting with an indicator that is initially dry because the moisture that must diffuse off the indicator to reach equilibrium is much greater than the moisture that would have had to diffuse onto a dry indicator to achieve equilibrium. Initially, this approach will provide a false moisture reading. Our experiments have shown, however, that this embodiment requires the user to leave the indicator in place for a minimum of 8 hours before inspection, the benefit of which is to significantly reduce manufacturing costs. Of course, every reasonable effort is made to keep the indicator as dry as practical during low-cost manufacturing to allow use of the indicator regardless of its initial state.

If the indicator indicates moisture after at least 1 day of exposure then it can be concluded that an unacceptable level of moisture above safe operating conditions is present in the refrigerant vapor. The refrigerant should then be dried by the installation or replacement of the filter/dryers.

A more accurate, but also somewhat more expensive, approach is to utilize a color chart (with the colors of different moisture or acid levels identified) adjacent to the indicator holder (e.g., sandwiched between the O-ring 12 and the indicator card 14) which is impregnated with the indicator chemical's color range. The user can then compare the equilibrium color of the indicator with the colors on the chart directly adjacent to the indicator to obtain an absolute moisture or acid level present in the system, rather than simply the fact that moisture or acid is present. Since our preferred embodiment is a low cost device and because any detectable moisture or acid means that a filter/drier should be added or replaced or other appropriate steps taken, we believe that the amount of moisture or acid present is not particularly important, rather just that moisture or acid has been found and should be treated. With current ARI refrigerant purity specifications at 10 PPM moisture by weight and 1 PPM acid by weight, our device will provide an excellent indication when the refrigerant is contaminated with moisture or acid. It is for this reason that our currently preferred embodiment does not include the color chart.

Figure 3:
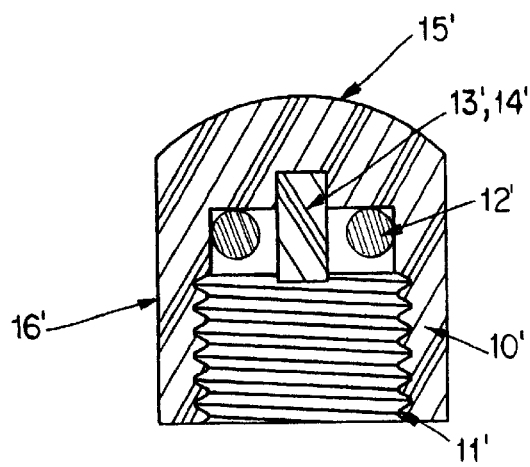
FIG. 3 is a view similar to FIG. 1 but of another embodiment where the valve core depressor is a porous material impregnated with the indicator formulation or material and fitted to the interior of the main structure.
Figure 7:
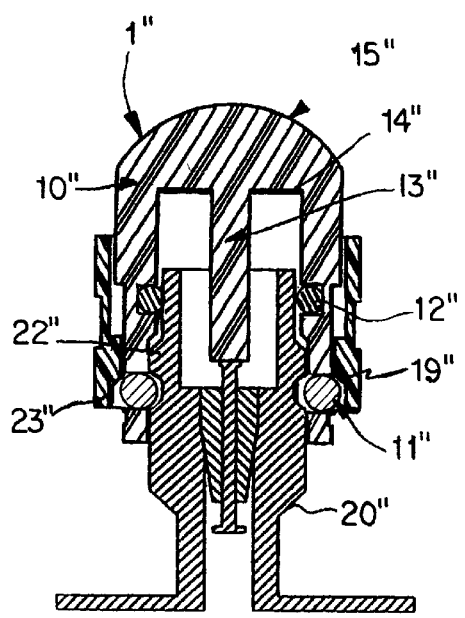
FIG. 7 is a view of the device shown in FIG. 6 installed on an automotive-type quick disconnect service valve which uses a Schrader valve.
Figure 8:
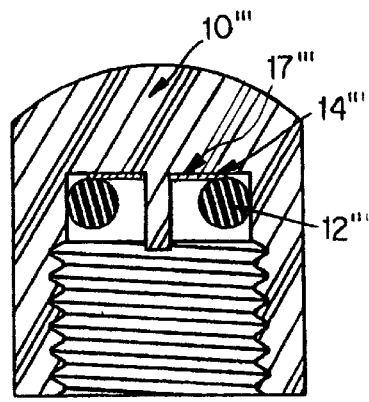
FIG. 8 is a view similar to FIG. 1, but with both a moisture indicating pad and a smaller diameter acid indicating pad sandwiched between the O-ring and the cap to indicate the presence of either moisture or acid.

Several other embodiments of indicators employing the principles of the present invention can be used as shown in FIGS. 3 and 7, where parts similar in function to the parts in FIG. 1 are designated by the same numerals but primed or double-primed. There are also several other standard moisture indicator chemicals, such as copper sulfate or other cobalt salts, which can be used for moisture testing and several other structures for holding the indicator chemicals including the use of porous rigid materials or an indicator paint. Alternatively, any standard moisture indicator can also be applied directly to the inside surfaces of the indicator cap 10.

Figure 6:
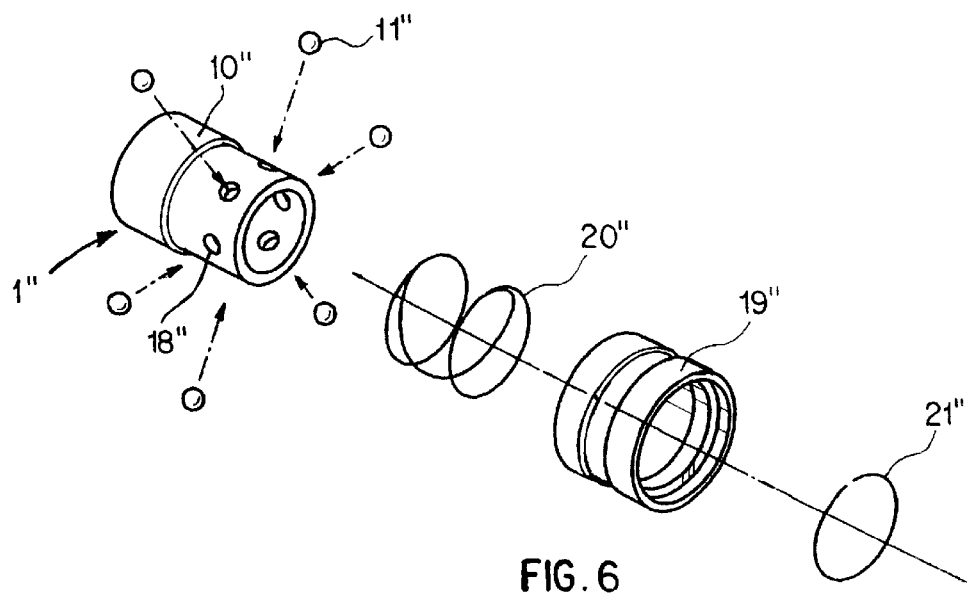
FIG. 6 is an exploded perspective view of another embodiment where the device is configured as a female automotive-type quick disconnect for connection to the low-side automotive service valve.

It is also within the contemplation of the present invention to place an acid indicating pad or paint layer 17''' (FIG. 9) along with the moisture indicating pad or paint layer 14''' in the cap 10''' so that one section can indicate the presence of acid and the other section can indicate the presence of moisture. The acid indicator chemical is selected from one of the following:

o-Cresolsulfonephthalein
m-Cresolsulfonephthalein
Thymolsulfonephthalein
Diphenylamino-p-benzene sodium sulfonate
2,6-Dinitrophenol
2,4-Dinitrophenol
Dimethylaminoazobenzene
Dimethylaminoazobenzene sodium sulfonate
Tetrabromophenolsulfone-phthalein
Tetrabromo-m-cresol-sulfonephthalein
o-Carboxybenzeneazo-dimethylaniline
Dichlorophenolsulfone-phthalein
Dibromo-o-cresolsulfone-phthalein
Dibromophenolsulfone-phthalein
p-Nitrophenol
Dibromothymolsulfone-phthalein
Aminodimethylaminotolu-phenazonium chloride
Phenolsulfonephthalein
m-Nitrophenol
o-Cresolsulfonephthalein
m-Cresolsulfonephthalein
Thymolsulfonephthalein
Phenolphthalein
a-Naphtholbenzein
Thymolphthalein
5-(p-Nitrophenylazo)-salicylic acid, Na salt
p-Sulfobenzeneazo-resorcinol
2,4,6-Trinitrophenyl-methylnitroamine The embodiment of FIG. 6 is substantially similar to the embodiment of FIG. 1 except a known quick disconnect fitting is used instead of a threaded connection. The quick disconnect comprises an indicator body 10'' which is provided with the O-shaped washer 12'' in a radial groove to provide a sealing connection with the outer surface of a service port 20''. Balls 11'' are disposed within holes 18'' distributed around the periphery of the outer wall of the body 10'' which operates with a sleeve-like member 19'' which rides over the outer wall and is biased toward the free end of the indicator 1'' by a compressor spring 20''. A retention washer. 21'' keeps the quick disconnect together. FIG. 7 shows how the embodiment of FIG. 6 has been installed on the male automotive-type quick disconnect service port 20'' which has a valve core which is depressed by the protrusion 13'' on the indicator 1''. The lower end of the indicator 1'' is placed over the service port 20'' and is pushed downwardly so that the sleeve 19'' moves upwardly relative to the indicator 1'' and balls 11'' are allowed to pass over a trapezoidal-shaped portion 22'' on the outer surface of the service port 20'' by virtue of the stepped portion 23'' on the inner surface of the sleeve 19''.

After fabrication, the indicator in each of the above-described embodiments is packaged in an airtight container (plastic bag, metal foil bag, glass container or metal container) to avoid unnecessary contamination prior to use.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A test device, comprising a cup-shaped member having impermeable transparent walls forming a solid enclosure with a single opening that Permits a sample to contact a moisture indicator by diffusion, said member being configured to activate only one service valve when connected therewith, and the moisture indicator being operatively located inside the member so as to be visible through the transparent walls.

2. The test device according to claim 1, wherein the moisture indicator is configured to operate by diffusion of moisture in a vapor phase of a working fluid.

3. The test device according to claim 1, wherein the single opening has standard internal threads to selectively retain the member at the service valve.

4. The test device according to claim 1, wherein the single opening provides a single connection point to the one service valve.

5. The test device according to claim 1, wherein the single opening has a standard automotive air conditioning quick disconnect fitting to removably and securely hold the member against the service valve.

6. The test device according to claim 1, further comprising a fixture having a service valve depressor to allow system working fluid access to the moisture indicator through the service valve.

7. The test device according to claim 1, wherein the member is a unitary rigid holder configured such that the moisture indicator extends along an interior transparent surface comprising one of the walls.

8. The test device according to claim 1, wherein the moisture indicator is directly deposited inside the member.

9. The test device according to claim 1, wherein the moisture indicator comprises a porous material at which a moisture indicator formulation has been deposited.

10. The test device according to claim 1, wherein the blind enclosure is comprised of a wall closing the one end of the member.

11. The test device according to claim 1, wherein the blind enclosure is configured to prevent passage of a working fluid from the one end.

12. The test device according to claim 1, wherein the member has a transparent portion associated with a region containing the moisture indicator.

13. The test device according to claim 12, wherein the transparent portion provides magnification.

14. The test device according to claim 1, wherein an acid indicator is operatively held within the member.

15. The test device according to claim 14, wherein the acid indicator is directly deposited inside the member.

16. The test device according to claim 1, wherein the moisture indicator consists of finely divided particles of cobalt salt prepared from a solution of at least one polymer and optionally at least one hygroscopic compound.

17. The test device according to claim 16, wherein the at least one polymer is selected from the group consisting of cellulose acetate, cellulose acetate butyrate, polyvinyl alcohol and polyamide polymers, and the at least one hygroscopic compound is selected from the group consisting of zinc chloride, calcium chloride, calcium chloride and, silica gel.

18. The test device according to claim 1, wherein the member contains a transparent lens configured to magnify a region thereof containing the moisture indicator.

19. The test device according to claim 18, wherein the member is hollow and has a protrusion extending toward the single opening to an extent necessary, when installed, to open the service valve constituted as a Schrader-valve.

20. The test device according to claim 19, wherein the protrusion comprises a rigid porous material impregnated with the acid indicator.

21. The test device according to claim 1, wherein the member is hollow and has a protrusion extending toward the single opening to an extent sufficient, when installed, to open the service valve constituted as a Schrader-valve.

22. The test device according to claim 21, wherein the protrusion is comprised of a rigid porous material impregnated with the moisture indicator.

23. The test device according to claim 22, wherein the protrusion is press-fit arranged in the member configured as a hollow threaded cap.

24. A method for detecting moisture in a vapor compression system working fluid, comprising the steps of inserting a viewable moisture indicator so as to be visible in a member having impermeable transparent walls forming a cavity and open at only one end in an operational state; and removably securing the member against only one service valve to activate the service valve and to permit the system working fluid substantially in the vapor phase to contact an interior portion of the member via diffusion.

25. A test kit, comprising a cup-shaped holder fixture having an opening at one end, and a moisture indicator operatively located interiorly of the holder fixture, with impermeable, transparent walls forming an enclosure of the fixture, said one end of said fixture being sized to provide a tight fit with a system service connection and configured to be selectively retained against and thereby activate a single service valve of the system service connection that permits a sample to contact the moisture indicator via diffusion.

26. The test kit according to claim 25, wherein said fixture comprises a protrusion in the opening for opening the service valve constituted as a Schrader-valve.

27. The test kit according to claim 26, wherein a protrusion extends through the single opening and is configured to open the service valve constituted as a Schrader-valve.

28. A test kit, comprising a cup-shaped holder fixture having an opening at one end thereof and an impermeable, transparent wall forming a cavity at another end thereof, and a moisture indicator operatively held within the holder fixture, said one end of said holder fixture being sized to provide a tight fit with a system service connection and configured to be held against a single vapor service valve to activate the latter that permits a sample to contact the moisture indicator via diffusion, and the holder fixture being configured to make the moisture indicator viewable in an area of said another end.

29. A test kit, comprising an impermeable, transparent cup-shaped rigid holder forming a solid enclosure, and a moisture indicator located inside the holder so as to be visible through the holder, said holder having an opening and being configured to be fastenable against a single system vapor service valve that permits a sample to contact the moisture indicator via diffusion.

30. The test kit according to claim 29, wherein the flat rigid holder has a protrusion projecting from the single opening through an aperture of the assembly to open the system service valve constituted by a Schrader-valve.

31. The test kit according to claim 29, wherein an acid indicator is operatively held within the holder.

32. A cup-shaped test device, comprising impermeable walls, at least one of which is transparent, the walls forming a cavity with a single opening that permits a sample to contact an acid indicator via diffusion, and the device being configured to be located relative to only one service valve whereby the service valve is actuatable by having said opening operatively connected therewith, and an assembly having said acid indicator operatively located relative to the at least one wall so as to be visible therethrough.

33. The test device according to claim 32, wherein the assembly is in contact with the wall.

34. A test device consisting of a member having a wall forming a cup-shaped blind enclosure at one end thereof, and a single opening at another end thereof to permit a sample to contact a sheet-shaped moisture indicator via a diffuser and configured to be located relative to a service valve, and an assembly having said sheet-shaped moisture indicator within the member and exposed to the single opening.

35. A test device, comprising a cup-shaped member having impermeable walls forming a sealed cavity with a single opening that permits a sample to contact the moisture indicator via diffusion and at least one transparent surface, and configured to be removably associated with a service valve, and said moisture indicator being located exclusively proximate the at least one transparent surface and exposed to the single opening so as to be exposable to moisture in a working fluid vapor phase entering through the single opening.

36. A test device consisting of a cup-shaped member having a single opening at one end for permitting a sample to contact a sheet-shaped indicator and for operative connection with a service valve with means for preventing a working fluid entering the member via the service valve from leaving the member, and an assembly having said sheet-shaped indicator operatively located within the member so as to be exposable to a diffused impurity consisting of at least one of moisture and acid in a vapor phase of the working fluid and viewable externally of the test device.

37. A test cap, comprising a cup-shaped member having an impermeable transparent wall forming a sealed enclosure and containing a sheet-shaped indicating substance, and further having an opening that permits a sample to contact the moisture indicator via diffusion configured to be removably associated with a service valve.

38. A test cap according to claim 37, wherein the indicating substance is a moisture indicating substance.

39. The test cap according to claim 37, wherein the indicating substance is an acid indicating substance.

40. The test cap according to claim 37, wherein the indicating substance is so arranged so as to be visible through the wall.

* * * * *